US010955941B2

United States Patent
Zipp et al.

(10) Patent No.: US 10,955,941 B2
(45) Date of Patent: Mar. 23, 2021

(54) MULTIMODAL INPUT DEVICE AND SYSTEM FOR WIRELESS RECORD KEEPING IN A MULTI-USER ENVIRONMENT

(71) Applicant: Atlantic Health System, Inc., Morristown, NJ (US)

(72) Inventors: Christopher P. Zipp, Morris Plains, NJ (US); Benjamin A. Bordonaro, Chester, NJ (US)

(73) Assignee: Atlantic Health System, Inc., Morristown, NJ (US)

( * ) Notice: Subject to any disclaimer, the term of this patent is extended or adjusted under 35 U.S.C. 154(b) by 0 days.

(21) Appl. No.: 16/549,173

(22) Filed: Aug. 23, 2019

(65) Prior Publication Data
US 2020/0310562 A1 Oct. 1, 2020

Related U.S. Application Data

(60) Provisional application No. 62/823,814, filed on Mar. 26, 2019.

(51) Int. Cl.
*G06F 3/0354* (2013.01)
*H04W 4/02* (2018.01)
(Continued)

(52) U.S. Cl.
CPC ........ *G06F 3/03545* (2013.01); *G06F 3/0346* (2013.01); *G06F 3/03543* (2013.01);
(Continued)

(58) Field of Classification Search
CPC ............. G06F 3/03545; G06F 3/03543; G06F 3/0346; G06F 2203/0381; G10L 15/26;
(Continued)

(56) References Cited

U.S. PATENT DOCUMENTS

| 5,991,431 A | 11/1999 | Borza et al. |
| 6,262,719 B1 | 7/2001 | Bi et al. |

(Continued)

FOREIGN PATENT DOCUMENTS

WO 2016/007188 A1 1/2016

OTHER PUBLICATIONS

Genius 2.4GHz Wireless Pen Mouse.
(Continued)

*Primary Examiner* — Ibrahim A Khan
(74) *Attorney, Agent, or Firm* — The McHattie Law Firm, LLC; William Smith

(57) ABSTRACT

A self-contained multimodal data input device for remotely entering data into a record-keeping system provides: wireless transmission and receipt of data; a pen-like profile; controls for emulating the left and right-click functions of a computer mouse and at least one command key of a standard keyboard; means for determining the orientation and movement, of the input device in space; and means for detecting at least one biometric characteristic of a user. In a system, the multimodal data input device connects and communicates with a gateway device according to the proximity of the input device to the gateway device in a many-to-many relationship. The system provides means for authenticating the input device and the user to the system by one-factor or two-factor authentication.

6 Claims, 4 Drawing Sheets

(51) Int. Cl.
*G08C 17/02* (2006.01)
*G06K 9/00* (2006.01)
*G06F 3/0346* (2013.01)
*G10L 19/00* (2013.01)
*G16H 10/60* (2018.01)
*H04L 29/06* (2006.01)
*G10L 15/22* (2006.01)
*G10L 15/26* (2006.01)

(52) U.S. Cl.
CPC ......... *G06K 9/00288* (2013.01); *G08C 17/02* (2013.01); *G10L 15/22* (2013.01); *G10L 15/26* (2013.01); *G10L 19/00* (2013.01); *G16H 10/60* (2018.01); *H04L 63/0861* (2013.01); *H04W 4/023* (2013.01); *G06F 2203/0381* (2013.01); *G10L 2015/223* (2013.01)

(58) Field of Classification Search
CPC ... G10L 19/00; G10L 15/22; G10L 2015/223; H04W 4/023; G08C 17/02; G06K 9/00288; G16H 10/60; H04L 63/0861
See application file for complete search history.

(56) References Cited

U.S. PATENT DOCUMENTS

| | | | |
|---|---|---|---|
| 6,539,101 B1 | 3/2003 | Black | |
| 6,741,729 B2 | 5/2004 | Bjorn et al. | |
| 6,924,790 B1 | 8/2005 | Bi | |
| 6,970,583 B2* | 11/2005 | Black | G07F 7/1008 |
| | | | 382/124 |
| 7,231,181 B2 | 6/2007 | Kohli et al. | |
| 7,385,595 B2* | 6/2008 | Bryborn | G06F 3/03545 |
| | | | 178/18.01 |
| 7,483,018 B2 | 1/2009 | Oliver | |
| 7,609,862 B2 | 10/2009 | Black | |
| 7,646,379 B1 | 1/2010 | Drennan et al. | |
| 7,733,326 B1 | 6/2010 | Adiseshan | |
| 8,907,782 B2 | 12/2014 | Baker et al. | |
| 9,201,523 B1* | 12/2015 | Hwang | G06F 3/0488 |
| 9,298,282 B2 | 3/2016 | Liberty | |
| 10,373,463 B1* | 8/2019 | Herring | G08B 13/1427 |
| 10,593,187 B2* | 3/2020 | Amir | G05B 15/02 |
| 10,613,666 B2* | 4/2020 | Bushnell | G06F 3/0346 |
| 10,622,101 B1* | 4/2020 | Dunlap | G16H 50/70 |
| 10,809,842 B2* | 10/2020 | Qiao | G06F 3/147 |
| 2001/0025289 A1 | 9/2001 | Jenkins et al. | |
| 2002/0126105 A1* | 9/2002 | O'Donnell, Jr. | G06F 3/03545 |
| | | | 345/179 |
| 2003/0220765 A1* | 11/2003 | Overy | H04W 12/003 |
| | | | 702/158 |
| 2004/0141015 A1 | 7/2004 | Fitzmaurice et al. | |
| 2008/0021741 A1* | 1/2008 | Holla | G16H 10/60 |
| | | | 705/3 |
| 2008/0166028 A1 | 7/2008 | Turek et al. | |
| 2008/0285626 A1 | 11/2008 | Claus et al. | |
| 2008/0303638 A1* | 12/2008 | Nguyen | G06Q 10/00 |
| | | | 340/10.42 |
| 2010/0052870 A1* | 3/2010 | King | G06F 13/385 |
| | | | 340/286.02 |
| 2011/0063094 A1 | 3/2011 | Meiertoberens et al. | |
| 2011/0090048 A1* | 4/2011 | Li | G06F 21/32 |
| | | | 340/5.82 |
| 2011/0128258 A1 | 6/2011 | Liang | |
| 2012/0221634 A1 | 8/2012 | Treu et al. | |
| 2013/0145420 A1* | 6/2013 | Ting | H04L 63/08 |
| | | | 726/1 |
| 2013/0191647 A1* | 7/2013 | Ferrara, Jr. | G06F 21/6245 |
| | | | 713/186 |
| 2013/0201162 A1* | 8/2013 | Cavilia | G06F 3/03545 |
| | | | 345/179 |
| 2013/0317848 A1* | 11/2013 | Savin | G16H 10/60 |
| | | | 705/3 |
| 2014/0145955 A1 | 5/2014 | Gomez et al. | |
| 2014/0180719 A1* | 6/2014 | Bell | G16H 10/60 |
| | | | 705/3 |
| 2014/0194817 A1* | 7/2014 | Lee | A61M 5/14228 |
| | | | 604/151 |
| 2014/0207686 A1* | 7/2014 | Experton | G06F 19/3418 |
| | | | 705/51 |
| 2015/0134358 A1* | 5/2015 | Fisher | G16H 10/65 |
| | | | 705/3 |
| 2015/0324078 A1* | 11/2015 | Dipin | G04G 21/04 |
| | | | 715/765 |
| 2016/0048718 A1* | 2/2016 | Apostolos | G06K 9/00087 |
| | | | 382/124 |
| 2019/0369755 A1* | 12/2019 | Roper | G06F 3/0481 |
| 2020/0081560 A1* | 3/2020 | Geller | G06F 1/3231 |

OTHER PUBLICATIONS

Pocket Mouse.
Penclic Mouse—Bluetooth 5-Button Ergonomic Mouse B2.
Ultra U12-40871 eXo Bluetooth Wireless Pen Mouse & Presenter.
Top 10 Best Wireless Pen Mouse in 2019 by Matthew on Pixelsmithstudios.com.

* cited by examiner

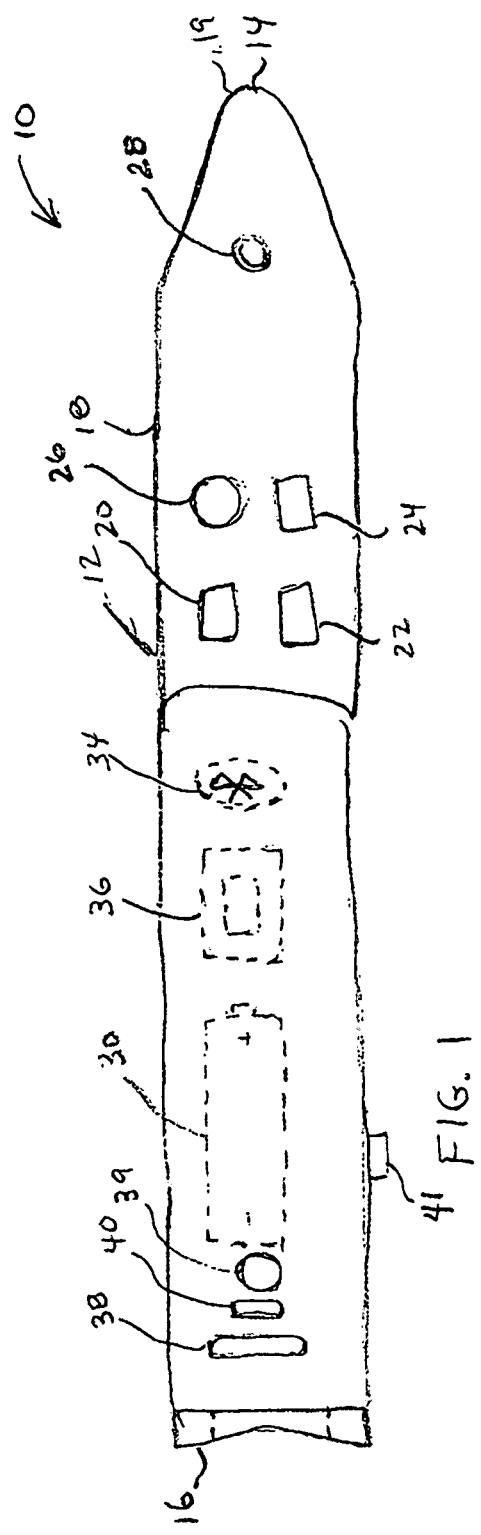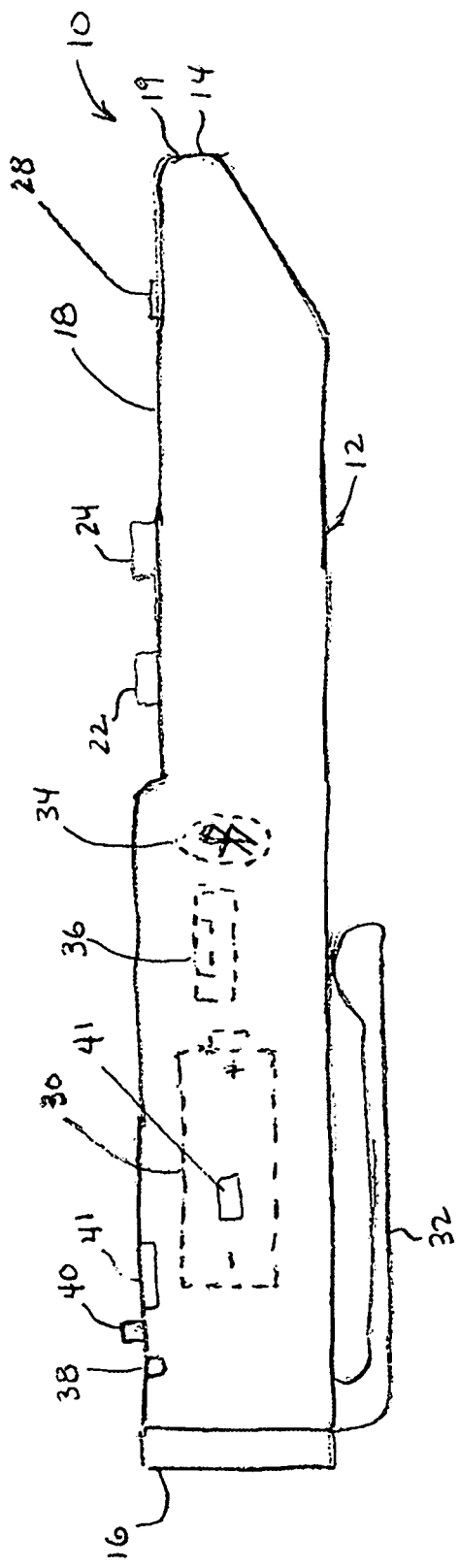

MULTIMODAL INPUT DEVICE AND SYSTEM FOR WIRELESS RECORD KEEPING IN A MULTI-USER ENVIRONMENT

TECHNICAL FIELD OF THE INVENTION

The present invention relates to the field of electronic devices for wireless input of data to data processing devices. The present invention further relates to the use of such electronic devices within multi-user recordkeeping systems.

BACKGROUND OF THE INVENTION

Electronic medical record (EMR) systems provide an electronic record of health-related information on an individual patient that can be shared among clinicians within a health care organization. Such electronic records are created, gathered, and managed through systems of data devices, such as desktop computers, tablets, and personal digital assistants, and are typically stored on systems of servers, whether on site or in remote locations (e.g., the "cloud"). EMR systems have the potential to facilitate workflow and improve the quality of patient care and safety, and doctor-patient interactions.

Despite technical developments that have taken place since the early 2010's, the existing clinical workflow of the EMR system still has numerous inefficiencies which take time and attention away from the practice of care. Typically, a clinician will interact with many patients or other health care consumers over the course of a workday, in many patient rooms, using many disparate workstations, input devices, and consulting rooms, or at a central location remote from the patient's location. In such arrangements, the clinician must position and orient him or herself at the device, manually log in at a keyboard, enter the patient's identifying information at a keyboard, and update the patient's records using a keyboard and/or mouse. In situations where the workstation is remote from the patient's room, some entry errors may be missed or information overlooked during the lag between interacting with the patient and reaching the workstation. In such cases, data might be entered by someone other than the clinician, thus increasing the possibility of lost or incorrectly entered data. In situations where the work station is in a fixed location in a patient's room or consulting room, the clinician may be distracted by moving back and forth between the patient and the workstation, or may interact with the patient from a seat at the workstation.

Some facilities mitigate the inefficiencies described above by using touch screens, or by using portable devices, such as laptop computers or tablets, which the clinician carries from room to room. Records may be stored on the device for download at a later time, or transmitted wirelessly to central servers at the time that it is collected. Even in such systems, it is still necessary for the clinician to interact with devices through the use of a mouse, keyboard or touch screen. It may often be necessary for the clinician to leave the portable device on a counter or table during the interaction, resulting in the same restrictions on the clinician's movement that result from using fixed workstations. Further, portable devices may be lost or stolen, putting the security of patient data at risk.

SUMMARY OF THE INVENTION

In a first aspect, the present invention provides a self-contained multimodal data input device for remotely entering data into a record-keeping system. Features of the input device include:

wireless transmission and receipt of data;
a pen-like profile;
controls for emulating the left and right-click functions of a computer mouse; controls for emulating at least one command key of a standard keyboard;
means for determining the orientation and movement of the input device in space for translation to X-Y coordinates for display on a monitor;
a self-contained power supply; and
controls for connecting and interrupting electrical connections between the power supply and electronic circuits in the input device.

In some embodiments, the input device further has one or more of the following features: means for programming the functions of the input device;
means for selecting and implementing pre-programmed commands;
means for uploading and storage of data from ancillary devices and means for downloading such data to other devices;
means for capturing and digitally encoding speech;
means for capturing and digitally encoding images; and
means for encoding a biometric characteristic of a person operating the input device.

In a second aspect, the present invention provides a system for connecting and disconnecting the input device and the gateway device according to the proximity of the input device to the gateway device. In an embodiment, the gateway device and input device maintain a communications channel between themselves according to a protocol for preventing other devices from hijacking of the channel. In an embodiment, each input device is capable of interacting with any gateway device in the system in a many-to-many relationship. In an embodiment, the protocol includes a step of pairing the input device with a gateway device until the input device is affirmatively disconnected from the gateway device.

In a third aspect, the present invention provides a system for authenticating the input device and/or the user of the input device to the EMR system. In one embodiment, the input device is authenticated by the gateway. In another embodiment, both the input device and the user are identified and verified (e.g., two-factor authentication). In an embodiment, the user is identified by a biometric parameter, such as a fingerprint image, a vocal pattern; or characteristics of a manual signature or visual image.

BRIEF DESCRIPTION OF THE DRAWINGS

For a better understanding of the present invention, reference is made to the following detailed description of the exemplary embodiments considered in conjunction with the accompanying drawings, in which:

FIG. 1 is a schematic top-down view of a multimodal input device according to an embodiment of the present invention;

FIG. 2 is a schematic left-side elevation view of the multimodal input device of FIG. 1;

DETAILED DESCRIPTION OF THE INVENTION

Figure 3:
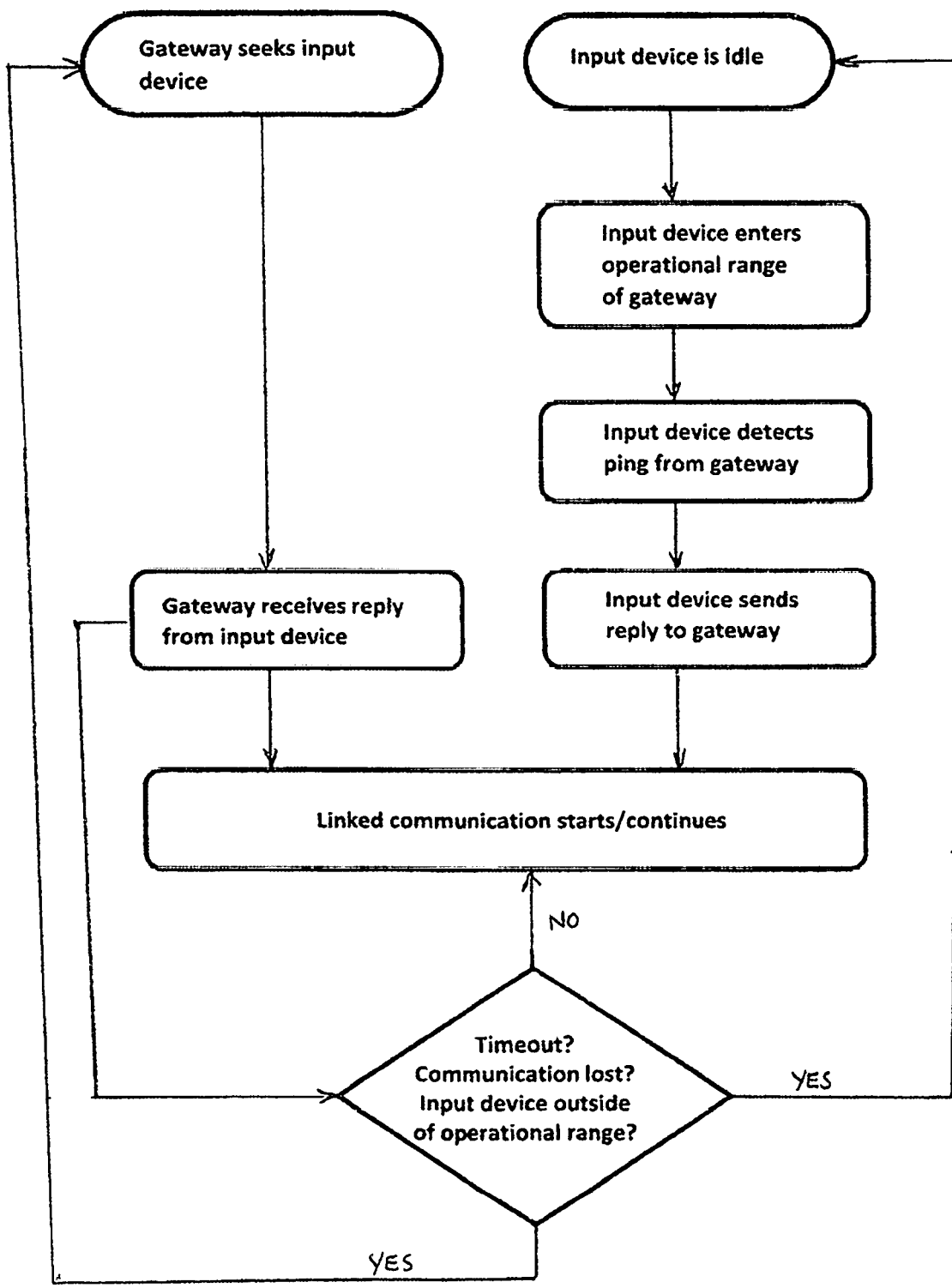
FIG. 3 is a schematic flowchart of a connection protocol for a multimodal input device and gateway device according to an embodiment of the present invention.

The present invention provides a multimodal data input device for entering data into a record-keeping system by wireless transmission. Such input devices may also capture physiological or status data transmitted wirelessly by nearby devices, or related by images or clinician's comments, and to download the data into gateway devices or the record-keeping system. The exemplary embodiments of the input device described herein allow a clinician to enter data into the record-keeping system from a patient's location, reducing the distractions and opportunities for error present with current data entry technology.

Embodiments of the input device may be operated as part of a system that includes gateway devices that are configured to exchange data with the input device, and to communicate with, control, or be controlled by computers and computer systems such as workstations, servers, and database management systems such as EMR systems. Such gateway devices may be provided as add-ons to a computer (e.g., a dongle), or may be an integral part of a computer. The gateway device may include software configured to perform the various data processing functions described herein, or such data processing functions may be distributed among the gateways, workstations, and or servers. The gateway devices and input devices are configured so that the associations of input devices and gateway devices are not limited, but operate in a many-to-many relationship.

Input Device

Referring to FIGS. 1 and 2, in an embodiment, the input device 10 is a hand-held self-contained wireless communication device having a pen-like profile. More specifically, the input device 10 includes a housing 12 having a distal end 14 and a proximal end 16 opposite the distal end 14, the housing 12 having a size and shape comparable to a writing pen. In the embodiment shown in FIGS. 1 and 2, the housing 12 is further provided with a substantially flat portion 18 on which controls 20, 22, 24, 26 are mounted, but an input device having a generally cylindrical housing without a flat portion 18 and/or having controls mounted on a rounded surface would also be within the scope of the invention. Embodiments of the input device 10 may also be provided with a stylus tip 19 at the distal end 14 of the input device 10.

The controls 20, 22, 24, 26 of the input device 10 of FIGS. 1 and 2 include a left click button 20 and a right click button 22, a command button 24, and a power on/off button 26. The input device 10 also includes a visible status indicator 28 (e.g., a LED) to indicate various operating states of the input device 10. The input device 10 is also provided with interconnected electronic circuits (not shown) for emulating the various functions controlled by the control buttons 20, 22, 24, 26. These functions include emulation of the left and right-click functions of a mouse as controlled by left and right click buttons 20, 22, emulation of a programmable command key of a conventional keyboard as controlled by command button 24, and connecting and interrupting a connection between a self-contained electrical power source 30 within the housing 12 and the various electrical circuits within the housing 12 by the power on/off button 26. Embodiments of input devices within the scope of the present invention may have more or fewer control or command buttons than those described herein, and may be equipped with electronic circuitry to enable more or fewer functions than those described in the present disclosure. Controls that may be used in the input devices of the present invention are not limited to buttons, and may include such controls as toggle switches, pressure sensors, temperature sensors, and sensors for detecting orientation and motion of the input device.

In an embodiment, the input device is provided with a clip 32 attached to the housing 12 for securing the input device 10 to other objects such as pads, clipboards, or pockets.

Further to the foregoing portion of the Detailed Description, an embodiment of the multimodal input device of the present invention includes digital data capture means for capturing digital data transmitted by other devices, digital data storage means for storing the captured digital data within the multimodal input device, and digital data transmission means for transmitting the stored captured digital data. Another embodiment of the multimodal input device of the present invention includes analog data capture means for capturing data other than digital data from the environment outside of the multimodal input device, digital data extraction means for extracting digital data from the captured analog data, digital data storage means for storing the extracted digital data, and digital data transmission means for transmitting the stored extracted data.

Continuing to refer to FIGS. 1 and 2, the input device 10 is provided with means for transmitting digital data, means for receiving digital data, means for storing digital data, and means for processing digital data. Means for capturing analog information (e.g., speech or images) and transforming such analog information to digital data may also be provided as components of embodiments of an input device within the scope of the present invention.

Continuing to refer to FIGS. 1 and 2, transmission and receipt of data is performed wirelessly by short-range wireless communication circuits 34 within the housing 12. The wireless communication device circuits are represented in FIGS. 1 and 2 (as well as in subsequent FIGS. 4 and 5) by the BLUETOOTH icon, which is a registered trademark of Bluetooth SIG, Inc., Kirkland, Wash. The use of this icon is for the purpose of example, and does not limit the type of wireless communication circuits or system that may be used in the present invention.

Continuing to refer to FIGS. 1 and 2, embodiments of the input device 10 are provided with programming means for programming the functions of the input device 10, which may include electronic means for uploading and installing computer code in the input device 10. An example would be electronic means for programming a command initiated by pressing command button 24. Programming means may also be provided for updating the software or firmware installed in the input device 10.

Continuing to refer to FIGS. 1 and 2, embodiments of the input device 10 are provided with means for selecting pre-programmed commands for transmission from the input device to a gateway device for processing or retransmission. Command button 24 and its associated electronic circuits (not shown) are a non-limiting example of a means for selecting pre-programmed commands. Additional command buttons and associated electronic means for selecting and implementing additional pre-programmed commands, may be provided in other embodiments of the input device of the present invention.

Continuing to refer to FIGS. 1 and 2, embodiments of the input device 10 are provided with means 36 for determining the orientation and motion of the input device 10 in space and for wirelessly communicating the orientation and movement of the input device 10 to a gateway device for translation to two-dimensional coordinates on a visual user interface. In an exemplary embodiment, means 36 for determining the orientation and motion of the input device include a combination of one or more of an accelerometer, gyroscope, and compass. In another embodiment, means 36 for determining the orientation and motion of the input device 10 includes an inertial measurement unit that operates along nine degrees of freedom.

Continuing to refer to FIGS. 1 and 2, embodiments of the input device 10 are provided with means for digitally encoding speech for transmission to a receiving device, such as a gateway, for translation into a code that is stored as text in a database (e.g., an EMR system) and/or displayed as text on a visual user interface. An example of such a means for digitally encoding speech would include a microphone such as microphone 38 and digital encoding circuits (not shown). The means for digitally encoding speech may also include an activation switch 40 for activating the microphone 38 and the digital encoding circuits, and for transmitting the encoded speech.

Continuing to refer to FIGS. 1 and 2, embodiments of the input device 10 are provided with means for digitally encoding visual images for transmission to a receiving device, such as a gateway, for translation into a code that is stored as an image file in a database (e.g., an EMR system) and/or displayed as an image on a visual user interface. An example of such a means for digitally encoding an image would include a microphone such as camera 39 and digital encoding circuits (not shown). The means for digitally encoding an image may also include an activation switch 41 for activating the camera 39 and the digital encoding circuits, and for transmitting the encoded speech.

Linking and Pairing Devices

Embodiments of the present invention provide a system for connecting and disconnecting the input device 10 and the gateway device according to the proximity of the input device 10 to the gateway device. Referring to FIG. 3, in an embodiment, the gateway device seeks an input device by transmitting a pulsed signal (a "ping"). In an embodiment, the operational range is the threshold distance at which an approaching input device detects the signal and transmits a reply that the gateway device detects. Upon detecting a reply from the input device, the gateway device and input device link to each other to establish a communication channel. In another embodiment, the gateway device monitors the power of the signal from the input device, and the link is established when the signal meets or exceeds a predefined power level. The gateway periodically checks for the presence of the linked input device within operational range. The link is maintained until a pre-specified event occurs, such as a timeout, a loss of communication, an active break in communication (e.g., the user operates a control on the input device to break the link), or the input device moves out of the operational range.

In an embodiment where multiple input devices are within the operational range, the gateway device maintains the first link established with an input device and does not link with other input devices until the first link is broken ("first come, first served"). Once the first link is broken, a different link may be established between the gateway device and a different input device.

In an embodiment, a pairing range is established within which the user can actively pair the gateway device and the input device. The threshold of the pairing range is nearer to the gateway device than the threshold of the operational range. In an embodiment, the user initiates pairing by operating a control on the input device while the input device is within the pairing range. In a further embodiment, the gateway device and the input device remain paired while the input device is within the operational range, until the link is actively broken by the user, or until a different input device pairs with the gateway while the first input device is outside of the operational range.

Interaction with Modal and Treatment Devices

Embodiments of the input device of the present invention provide means for uploading and storing data from modal devices used to monitor or record a patient's physiological condition, then downloading such data to a gateway or other digital device. Such devices may include, without limitation, body temperature sensors, heartbeat monitors, blood pressure monitors, respiration monitors, and the like which record data in a digital form. In an embodiment, operational data may also be uploaded from treatment devices that are used to treat a patient (e.g., pumps for intravenous injection or CPAP devices). In such embodiments, the input device and modal or treatment device are arranged to cooperate in the transfer of data. Each modal or treatment device may be provided with its own operational and/or pairing device, which cooperate with multiple input devices in substantially the same manner as described above with regard to gateways and input devices. In an embodiment, data upload may be initiated by moving an input device into the operational range of a modal or treatment device and operating a control (e.g., a button, sensor, or switch) on the input device. In another embodiment, data transfer is initiated by tapping or otherwise physically contacting the input device with the modal device or treatment device. Uploaded data is stored in memory devices within the input device, and downloaded from memory to a gateway or other device when the input device is within operating range of the device that is to receive the downloaded data. Download is initiated by operating a control on the input device or by tapping or other physical contact between the input device and the receiving device, according to protocols similar to those used to initiate an upload of data to the input device. Both upload and download of data may be performed using single or multiple buffering.

Authentication of Input Devices and Users

Embodiments of the present invention provide systems for authenticating the input device and/or the user of the input device to the gateway device alone or to the larger system in which the gateway operates. For the purpose of the present disclosure, authentication includes steps of identifying the device and/or user, then verifying that the input device and/or its user is authorized to interact with the EMR system. In one embodiment, the input device transmits an encoded signal that is unique to the input device, and the gateway device or a processor in communication with the gateway device compares the encoded signal to records of registered input devices to determine whether the encoded signal corresponds to a registered input device. If the input device is a registered device, the gateway device then determines whether the input device is authorized to interact with the EMR system. Appropriate pre-defined actions are then taken. Appropriate pre-defined actions may include, without limitation, authorizing access if the device is successfully authenticated and terminating the communication link if the device is not successfully authenticated.

In another embodiment, both the input device and its user are identified and verified in a two-factor authentication protocol. In an embodiment, the user is identified by biometric data unique to the user. Examples of biometric data include, without limitation, a fingerprint, a voiceprint, an image, or a handwritten signature.

Figure 4:
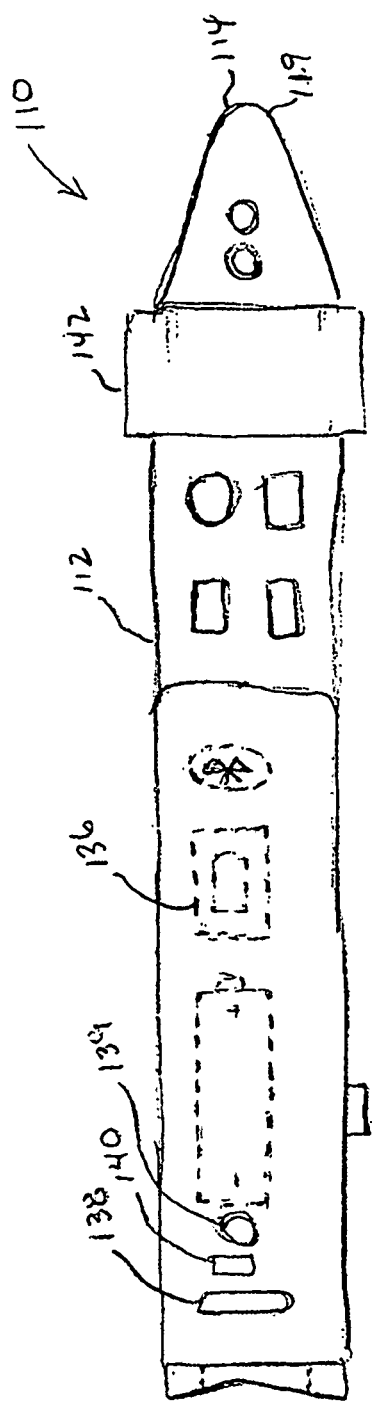
FIG. 4 is a schematic top-down view of a second embodiment of the multimodal input device of the present invention.
Figure 5:
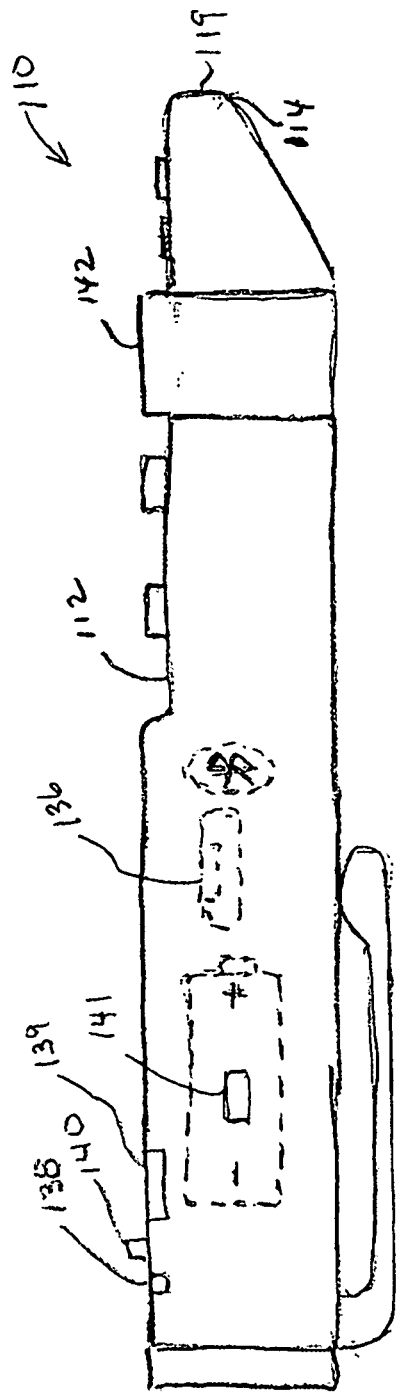
FIG. 5 is a schematic left-side elevation view of the multimodal input device of FIG. 3.

In embodiments in which a user is to be identified by a fingerprint, an input device 110 is equipped with a fingerprint scanner 142 near the distal end 114 of the pen-like housing 112 (see FIGS. 4 and 5). The user presses his finger on the fingerprint scanner 142, which encodes data describing the fingerprint (an "encoded image") and transmits the encoded image to the gateway device for identification of the user and verification of the user's authorization to access the EMR system.

For embodiments in which the user is to identified by a voiceprint, the input device 110 is equipped with a means for digitally encoding speech, which may include a microphone 138 and electronic digital encoding circuits. The user speaks a keyword or phrase into the microphone 138, and the spoken keyword or phrase is encoded into a digital voiceprint. The digital voiceprint is then transmitted to the gateway device for identification of the user and verification of the user's authorization to access EMR system.

In embodiments in which a user is to be identified by a visual image fingerprint, an input device 110 is equipped with a camera 139 near the proximal end 116 of the pen-like housing 112 (see FIGS. 4 and 5). For facial recognition, the user looks into the camera 139, and electronic circuitry within the pen extracts and encodes data regarding selected features of the image. The input device 110 transmits the encoded data to the gateway device for comparison with a set of encoded data files to identify the user and verify the user's authorization to access the EMR system.

In embodiments in which a user is to be identified by a signature, an input device 110 is equipped with means 136 for determining the orientation and motion of the input device 110 (see FIGS. 4 and 5). A further discussion of means for determining orientation and motion of an input device is provided above in regard to means 36 of FIGS. 1 and 2. For the purpose of this disclosure, a "signature" is not limited to a user's name, but includes any combination of symbols and/or motions unique to the user. In an embodiment, the user moves the input device as if writing the signature, and the motion is converted to digital data by the means 136 for detecting motion and orientation of the input device 136 and related circuitry in the input device 136. The digital data is encoded and transmitted to the gateway device for identification of the user and verification of the user's authorization to access the EMR system. The user may make the signature by moving the pen in three-dimensions in free space, or contact the stylus 119 to a surface while making the signature to simulate handwriting. In an embodiment, the stylus 119 may be provided with a pressure sensor (not shown) to measure changes in the pressure exerted on the stylus over time. In an embodiment of the present invention, the pressure data is encoded with the motion and orientation data.

Figure 6:
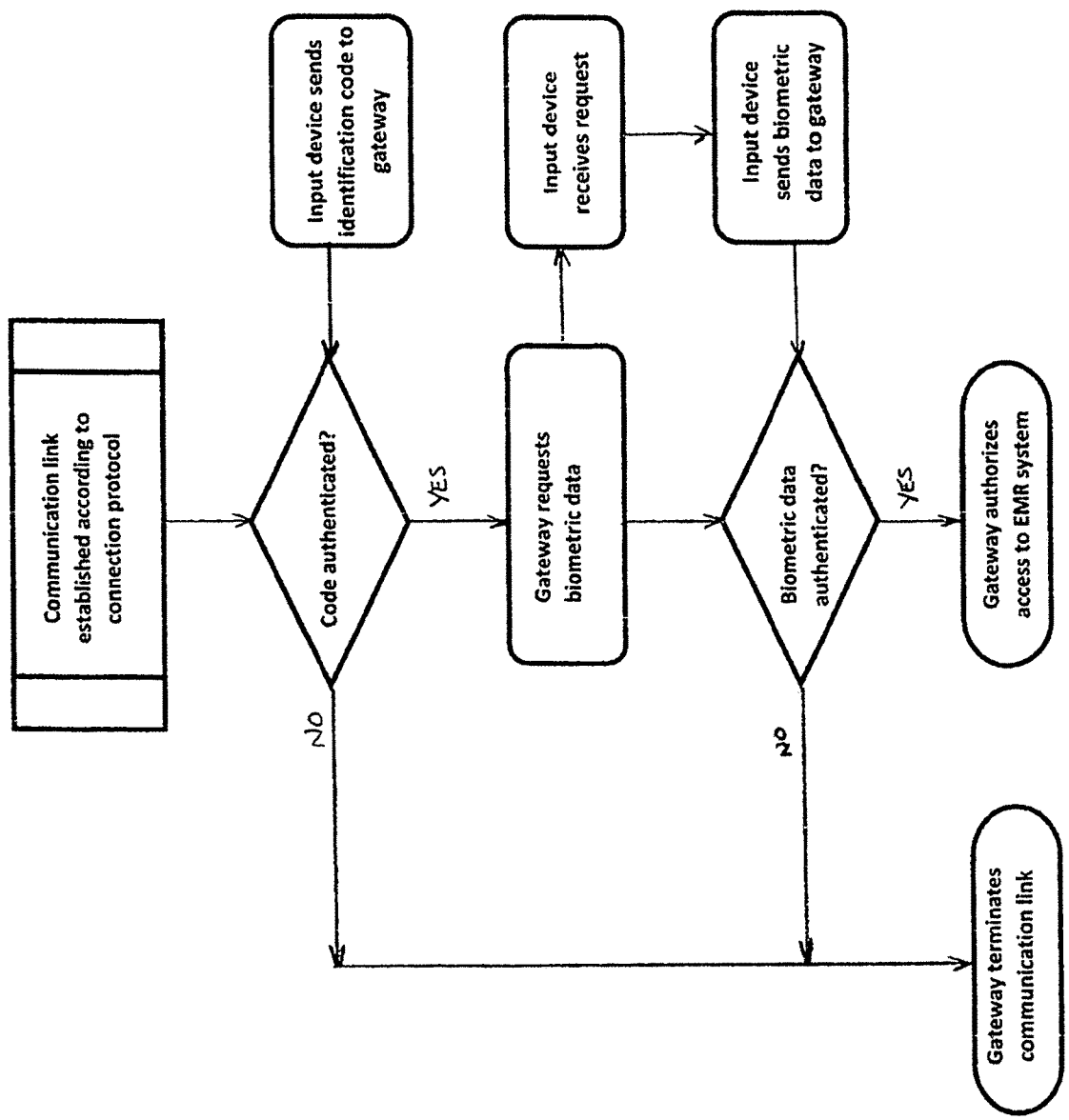
FIG. 6 is a schematic flowchart of an authentication process according to an embodiment of the present invention.

FIG. 6 presents a flowchart illustrating an exemplary embodiment of a two-factor authorization process according to the present invention. In the exemplary process of FIG. 6, a communication link is established between the gateway device and the input device according to a predetermined connection protocol (e.g., the protocol discussed above with respect to FIG. 3). The input device is identified and verified as discussed above. If the input device is not successfully authenticated, the communication link between the gateway device and the input device is terminated. If the input device is successfully authenticated, the gateway requests the input device to transmit the user's biometric data. The input device receives the request and transmits the biometric data (e.g., the fingerprint image or voiceprint discussed above. The gateway device, or a processor in communication with the gateway device, compares the biometric data against a list of data records to identify the user and verify that the user is authorized to access the EMR system. If the input device is not successfully authenticated, the communication link between the gateway device and the input device is terminated. If the input device is successfully authenticated, the user is authorized to use the input device to access the EMR system.

In an embodiment of the present invention, the input device is registered to only one user. In an exemplary embodiment, a reference copy of the biometric data is stored on the input device, and the comparison of the user's fingerprint image or voiceprint with the reference copy is made at the input device. The input device then transmits a MATCH or NO MATCH signal to the gateway device, which initiates the appropriate pre-defined actions.

In an embodiment of the present invention, the input device is provided with the necessary components to collect and transmit more than one type of biometric data. In an embodiment, a second biometric characteristic may be used to authenticate a user if the use of a first biometric characteristic is unsuccessful. In an embodiment, more than one biometric characteristic may be required by the authentication protocol.

In an embodiment of the present invention, a user that has a registered input device, but fails or does not perform the second part of the two-factor authentication process, has partial access to the gateway and/or other parts of the system for limited purposes. In an exemplary embodiment, a user with partial access may display data stored in the input device, such as uploaded data or visual images captured by the camera.

Once the device and/or user have been verified, the user can interact with the EMR system using the input and data processing functions programmed into the input device, as guided by an audio or visual user interface. EMR systems are typically constructed from proprietary software which may not include the functions needed to interact with the input device. In such EMR systems, one or more gateways or software modules must be added to the EMR system to interact with the input device and mediate communications between the input device and the EMR system.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention as embodied in the appended claims.

The invention claimed is:

1. A method for maintaining wireless communication links between multiple multimodal input devices and multiple remote computers, each multimodal input device and remote computer configured to act as a device for receiving wireless signals and as a device for transmitting wireless signals, wherein each multimodal input device and each remote computer has its respective digital data capture means for capturing digital data transmitted wirelessly by other devices, respective first memory for storing the captured digital data transmitted wirelessly by the other devices within the multimodal input device or remote computer, respective digital data transmission means for wirelessly transmitting stored captured digital data, and respective means for detecting wireless signals and determining the distance between the receiving device and the transmitting device, each multimodal input device further including a user-data input device, data capture means for capturing user data from the user-data input device, second memory for storing the captured user data, digital data extraction means, data encoding means for encoding data into a digital record, third memory for storing digital records, circuitry for storing and retrieving records from a database of reference user-identification records, and a stored database of reference user-identification records, wherein the user-data input device receives data provided by the user, wherein the method includes the following steps performed at a first multimodal input device:

capturing from the user-data input device user-identification data provided by the user, the data captured by the data capture means;

extracting digital data from the captured user-identification data by the digital data extraction means;

encoding the extracted digital data as an encoded user-identification record by the data encoding means;

storing the encoded user-identification record in the third memory for storing digital records;

comparing the encoded digital user-identification record to digital reference user-identification records stored in the database of reference user-identification records; and if the encoded user-identification record matches a reference user-identification record, encoding and storing a user-status code having a GO value to indicate that the user has been identified, else encoding and storing a user-status code having a NOGO to indicate that the user has not been identified, the method including the further steps of the remote computers sending repeated signals requesting responses from multimodal input devices until a first multimodal input device responds with a signal acknowledging the request from a first remote computer;

upon receiving the response from the first multimodal input device, the first remote computer initiates a first series of predetermined actions to estimate the distance between the first remote computer and the first multimodal device;

if the estimated distance is less than a first threshold distance, then the first remote computer initiates a communication link with the first multimodal input device;

the first multimodal input device transmits the user-status code to the first remote computer when the first multimodal input device sends the signal acknowledging the request from the first computer, and wherein if the user-status code has a NOGO value, then the first computer breaks the communication link;

else the first multimodal input device continues to estimate the distance between the first remote computer and the first multimodal input device, and breaks the communication link if one or more of the following conditions occurs: (i) the distance between the first remote computer and the first multimodal device is greater than the first threshold distance, (ii) the first remote computer no longer receives a response from the first multimodal device, (iii) the remote computer receives a command to break the communication link, and (iv) the remote computer or multimodal input device is deactivated.

2. The method of claim 1, wherein the user-data input device includes one or more of a position-detection means for determining the orientation and/or motion of the input device, speech-capturing means for digitally capturing speech, and image-capturing means for digitally capturing an image.

3. The method of claim 1, wherein the first multimodal input device includes a command-key means for transmitting a signal to initiate pairing of the first multimodal input device and the first remote computer and for breaking the pairing, said method including the further step of initiating pairing of the first multimodal device by the command-key means, wherein pairing occurs only if the estimated distance is less than the first estimated distance.

4. A method for maintaining wireless communication links between multiple multimodal input devices and multiple remote computers, each multimodal input device and multiple remote computer configured to act as a device for receiving wireless signals and as a device for transmitting wireless signals, wherein each multimodal input device and each remote computer has its respective digital data capture means for capturing digital data transmitted wirelessly by other devices, respective first memory for storing the captured digital data transmitted wirelessly by the other devices within the multimodal input device or remote computer, respective digital data transmission means for wirelessly transmitting stored captured digital data, and respective means for detecting wireless signals and determining the distance between the receiving device and the transmitting device, each multimodal input device further including a user-data input device, data capture means for capturing user data from the user-data input device, digital data extraction means, data encoding means, and third memory for storing the digital records, circuitry for storing and retrieving records from a database of reference user-identification records, and a stored database of reference user-identification records, wherein the user-data input device receives data provided by the user, wherein the method includes the following steps performed at a first multimodal input device:

capturing from the user-data input device user-identification data provided by the user, the data captured by the data capture means;

extracting digital data from the captured user-identification data by the digital data extraction means;

encoding the extracted digital data as an encoded user-identification record by the data encoding means;

storing the encoded user-identification record in the third memory for storing digital records;

comparing the encoded digital user-identification record to digital reference user-identification records stored in the database of reference user-identification records; and if the encoded user-identification record matches a reference user-identification record, encoding and storing a user-status code having a GO value to indicate that the user has been identified, else encoding and storing a user-status code having a NOGO to indicate that the user has not been identified, the method including the further steps of the remote computers sending repeated signals requesting responses from multimodal input devices until the first multimodal input device responds with a signal acknowledging the request from a first remote computer, the signal including the user-status code, thereby initiating a communication link between the first remote computer and the first multimodal input device;

if the user-status code has a NOGO value, then the first computer breaks the communication link, else the first remote computer determines whether there is another multimodal input device already in communication with the first remote computer, if so, breaking the communication link with the first multimodal input device, and if not then initiating a first series of predetermined actions to estimate the distance between the first remote computer and the first multimodal device; and if the estimated distance is less than a first threshold distance, the first remote computer maintains the communication link with the first multimodal input device then continues to estimate the distance between the first remote computer and the first multimodal input device, and breaks the communication link if one or more of the following conditions occurs: the distance between the first remote computer and the first multimodal device is greater than the first threshold distance, the first remote computer no longer receives a response from the first multimodal device, the remote computer receives a command to break the communication link, and the remote computer or multimodal input device is deactivated.

5. The method of claim 4, wherein the user-data input device includes one or more of a position-detection means for determining the orientation and/or motion of the input device, speech-capturing means for digitally capturing speech, and image-capturing means for digitally capturing an image.

6. The method of claim 4, wherein the first multimodal input device includes a command-key means for transmitting a signal to initiate pairing of the first multimodal input device and the first remote computer and for breaking the pairing, said method including the further step of initiating pairing of the first multimodal device by the command-key means, wherein pairing occurs only if the estimated distance is less than the first estimated distance.

* * * * *